United States Patent
Kleen et al.

(10) Patent No.: US 6,787,128 B2
(45) Date of Patent: Sep. 7, 2004

(54) STRUCTURE-IMPROVING HAIR CARE AGENTS

(75) Inventors: Astrid Kleen, Erkrath (DE); Frank Naumann, Duesseldorf (DE); Horst Hoeffkes, Duesseldorf (DE); Oliver Brabaender, Oberhausen (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 10/314,098

(22) Filed: Dec. 6, 2002

(65) Prior Publication Data

US 2003/0113280 A1 Jun. 19, 2003

Related U.S. Application Data

(63) Continuation of application No. PCT/EP01/06557, filed on Jun. 9, 2001.

(30) Foreign Application Priority Data

Jun. 20, 2000 (DE) .......................................... 100 30 313
Apr. 26, 2001 (DE) .......................................... 101 20 306

(51) Int. Cl.$^7$ .............................................. A61K 7/075
(52) U.S. Cl. ..................... 424/70.1; 424/70.2; 514/277; 514/257
(58) Field of Search .............................. 424/70.1, 70.2, 424/70.27; 514/277, 357

(56) References Cited

U.S. PATENT DOCUMENTS 4,201,235 A    5/1980  Ciavatta
4,210,654 A    7/1980  Bauer et al.
5,681,554 A   10/1997  Cannell et al.
5,833,998 A * 11/1998  Biedermann et al. ....... 424/401

FOREIGN PATENT DOCUMENTS

| DE | 196 13 567 A1 | 10/1997 |
| EP | 0 001 079 B1 | 7/1981 |
| EP | 0 678 293 A2 A3 | 10/1995 |
| WO | WO 98/51265 A1 | 11/1998 |

OTHER PUBLICATIONS

Merck Index, Compounds, 7878, 7879,7880,7881 and 7882(1983).*

F. Schwenker et al., "Differential Thermal Analysis of Protein Fibers", Textile Research Institute, Princeton, New Jersey, vol. 30, p. 800–801 (1960).

W. D. Felix et al., The Differential Thermal Analysis of Natural and Modified Wool and Mohair, vol. 33, p. 465 (1963).

F. J. Wortmann et al., Characterizing Keratins Using High-Pressure Differential Scanning Calorimetry (HPDSC), Journal of Applied Polymer Science, vol. 48, pp. 137–150 (1993).

* cited by examiner

Primary Examiner—Jyothsna Venkat
(74) Attorney, Agent, or Firm—Stephen D. Harper; Gregory M. Hill

(57) ABSTRACT

There are provided topical hair care compositions for improving the structure and strength of hair keratin and the fastness to washing of hair colors which contain vitamin B6 derivatives of the formula (1) or physiologically compatible salts thereof.

5 Claims, No Drawings

STRUCTURE-IMPROVING HAIR CARE AGENTS

CROSS REFERENCE TO RELATED APPLICATIONS

This application is a continuation under 35 U.S.C. §365 (c) and §120 of international Application No. PCT/EP01/06557 filed Jun. 9, 2001 and under §119 of German Application No. 100 30 313.7 filed Jun. 20, 2000 and German Application No. 101 20 306.3 filed Apr. 26, 2001.

SUMMARY OF THE INVENTION

This invention relates to the use of compounds belonging to the group of vitamin B6 and derivatives thereof for improving the structure and strength of hair keratin and the fastness to washing of hair colors in preparations for topical application.

BACKGROUND OF THE INVENTION

Hair keratin is structurally damaged by regular treatment with alkaline, strongly reducing or oxidizing chemicals, for example in permanent waving, coloring or bleaching of the hair. Such damage is reflected in a weight loss, in a reduction in the melting point of the keratin and in increasing fragility, poor combability and a deterioration in the hold and body of the hair. In addition, structurally damaged hair is often dull and lackluster in appearance.

To overcome this drawback, structure-improving additives, for example formaldehyde and formaldehyde donors, S-acetyl succinanhydride, ammonium vinyl phosphonate, ammonium phosphate, boric acid, oxazolidines, reducing sugars, tocopherols or so-called onic acids (for example gluconic acid), have already been added to hair-care preparations. Although such additives are effective to a certain extent, their effect on seriously damaged hair is still unsatisfactory. Accordingly, there was still a need to find structure-improving additives for hair which would be suitable for treating the hair after permanent waving or coloring processes.

Pyridoxine (pyridoxol) and other compounds belonging to the vitamin B6 group have already been proposed for use in hair tonics for reducing refatting and for stimulating hair growth.

EP 0678293 A2 proposes topical compositions containing pyridoxine tripropionate for treating the hair and skin. EP 001079 A1 describes describes anti-seborrheic cosmetic compositions containing pyridoxine tripalmitate as their active ingredient.

DESCRIPTION OF THE INVENTION

The present invention relates to the use of vitamin B6 derivatives corresponding to formula (I):

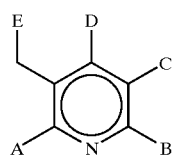

(I)

in which

A and B independently of one another represent hydrogen, halogen, a $C_{1-4}$ alkyl group, a $C_{3-6}$ cycloalkyl group, a $C_{1-4}$ monohydroxyalkyl group, a $C_{2-4}$ oligohydroxyalkyl group, a $C_{1-4}$ aminoalkyl group, a group —OR or a group —NR$^1$R$^2$, where R$^1$ and R$^2$ independently of one another represent hydrogen, a $C_{1-4}$ alkyl group or a $C_{1-4}$ monohydroxyalkyl group or R$^1$ and R$^2$ together with the nitrogen atom form a saturated ring, C represents a group —OR, —NR$^1$R$^2$, —OP(O)(OR$^3$)$_2$, a $C_{1-4}$ monohydroxyalkyl group, a $C_{2-4}$ oligohydroxyalkyl group or a $C_{1-4}$ alkyl group, D represents a group —OR, a carboxy group, a $C_{1-22}$ alkoxycarbonyl group, a formyl group, a group —CH$_2$OR or a group —CH$_2$—NR$_2$, E represents a group —OR, —OP(O)(OR$^3$)$_2$, a $C_{1-4}$ monohydroxyalkyl group or a $C_{2-4}$ oligohydroxyalkyl group, R representing hydrogen, a $C_{1-4}$ alkyl group, a $C_{1-22}$ acyl group, a hydroxy-$C_{2-22}$-acyl group, a $C_{2-10}$ carboxyacyl group, a $C_{3-10}$ oligocarboxyacyl group, an oligocarboxymonohydroxy-$C_{3-10}$-acyl group, an oligocarboxyoligohydroxy-$C_{3-10}$-acyl group, a $C_{3-8}$ cycloalkyl group, a $C_{1-4}$ monohydroxyalkyl group, a $C_{2-4}$ oligohydroxyalkyl group, an aryl group which may contain a hydroxy, nitro or amino group, a heteroaromatic group or a group —CH$_2$CH$_2$NR$^1$R$^2$, where R$^1$ and R$^2$ are as defined above, R$^3$ representing hydrogen or a $C_{1-5}$ alkyl group, or one of the corresponding physiologically compatible salts, for improving the structure and strength of hair keratin and the fastness to washing of hair colors by topical application of preparations containing these derivatives/salts.

Compounds corresponding to formula (I) in which one of the two groups A and B is hydrogen are preferred.

Compounds corresponding to formula (I) in which one of the two groups A and B is hydrogen and the other group is a $C_{1-4}$ alkyl group are preferred.

Other preferred compounds of formula (I) are those in which C is a hydroxy group, a $C_{1-4}$ monohydroxyalkyl group or a $C_{2-4}$ oligohydroxyalkyl group.

According to the invention, compounds of formula (I) in which D is a hydroxymethyl group, a hydroxy group, a carboxy group, a group —CH$_2$—NR$_2$ or a formyl group are preferred.

Other preferred compounds of formula (I) are those in which E is a hydroxy group or a group —OP(O)(OH)$_2$.

Particularly preferred compounds corresponding to formula I are pyridoxine (A=H, B=CH$_3$, C=OH, D=CH$_2$OH, E=OH), pyridoxal (A=H, B=CH$_3$, C=OH, D=CHO, E=OH), pyridoxal-5'-phosphate (A=H, B=CH$_3$, C=OH, D=CHO, E=OP(O)(OH)$_2$) and pyridoxamine (A=H, B=CH$_3$, C=OH, D=CH$_2$NH$_2$, E=OH).

Examples of $C_{1-4}$ alkyl groups in the compounds according to the invention are methyl, ethyl, n-propyl, isopropyl, n-butyl and tert butyl. Preferred alkyl groups are methyl and ethyl. Methyl is a particularly preferred alkyl group. Preferred $C_{3-6}$ cycloalkyl groups are cyclopropyl, cyclobutyl, cyclopentyl, cyclohexyl. Cyclohexyl and cyclopentyl are particularly preferred groups. Preferred $C_{1-4}$ monohydroxyalkyl groups are the groups hydroxymethyl, 2-hydroxyethyl, 3-hydroxypropyl or 4-hydroxybutyl; hydroxymethyl and 2-hydroxyethyl are particularly preferred monohydroxyalkyl groups. A preferred $C_{2-4}$ oligohydroxyalkyl group is the 1,2-dihydroxyethyl group. Preferred $C_{1-22}$ acyl groups are, for example, acetyl, propionyl, butyryl, valeryl, capryl, lauryl, myristyl, palmityl, stearyl, linolyl, behenyl. Examples of a hydroxy-$C_{2-22}$-acyl group are salicylic acid or lactic acid. Preferred $C_{2-10}$ carboxyacyl groups are derived, for example, from malonic acid, succinic acid or adipic acid.

One example of a preferred $C_{3-10}$ oligocarboxyacyl group is glyceric acid. A preferred oligocarboxymonohydroxy-$C_{3-10}$-acyl group is derived, for example, from citric acid or malic acid. Preferred oligocarboxyoligohydroxy-$C_{3-10}$-acyl groups are derived, for example, from tartaric acid. According to the invention, preferred halogen substituents are fluorine, chlorine, bromine and iodine; chlorine and bromine are particularly preferred. Physiologically compatible salts in the context of the invention are salts of inorganic or organic acids, for example hydrochlorides, sulfates or hydrobromides. According to the invention, the other terms used are derived from the definitions given here.

The ester derivatives of the compounds corresponding to formula (I) also have physiological and hair-structure-improving properties. This applies in particular to the esters of pyridoxine which can be converted by hydrolysis into pyridoxine. In addition, the ester derivatives acquire improved lipid solubility compared with the non-esterified derivatives. Other examples of carboxylic acid ester derivatives of pyridoxine are derived from the carboxylic acids, such as formic acid, acetic acid, propionic acid, butyric acid, isobutyric acid, valeric acid, isovaleric acid, pivalic acid, oxalic acid, malonic acid, succinic acid, glutaric acid, glyceric acid, glyoxylic acid, adipic acid, pimelic acid, suberic acid, azelaic acid, sebacic acid, propiolic acid, crotonic acid, isocrotonic acid, elaidic acid, maleic acid, fumaric acid, muconic acid, citraconic acid, mesaconic acid, camphor acid, benzoic acid, o,m,p-phthalic acid, naphthoic acid, toluylic acid, hydratropic acid, atropic acid, cinnamic acid, isonicotinic acid, nicotinic acid, bicarbamic acid, 4,4'-dicyano-6,6'-binicotinic acid, 8-carbamoyloctanoic acid, 1,2,4-pentanetricarboxylic acid, 2-pyrrole carboxylic acid, 1,2,4,6,7-naphthalene pentaacetic acid, malonaldehydic acid, 4-hydroxyphthalamidic acid, 1-pyrazole carboxylic acid, gallic acid or propane tricarboxylic acid, and from dicarboxylic acids selected from the group consisting of compounds corresponding to general formula (II):

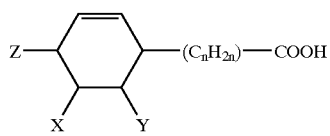

(II)

in which Z represents a linear or branched alkyl or alkenyl group containing 4 to 12 carbon atoms, n is a number of 4 to 12 and one of the two groups X and Y represents a COOH group and the other represents hydrogen or a methyl or ethyl group, dicarboxylic acids corresponding to general formula (II) which additionally contain 1 to 3 methyl or ethyl substituents on the cyclohexene ring and dicarboxylic acids which formally are formed from the dicarboxylic acids (II) by addition of one molecule of water onto the double bond in the cyclohexene ring.

The structure-improving effect of the vitamin B6 derivatives on hair keratin can be quantitatively determined by high-pressure differential scanning calorimetric measurements (HP-DSC) of the keratin melting behavior (cf. Examples). The improvement in the fastness of the hair to washing can be quantitatively determined by colormetric measurement of the color difference between colored, unwashed hair and colored, repeatedly washed hair. These effects are particularly noticeable when seriously damaged hair is treated with a composition containing vitamin B6 derivatives. Hair is seriously damaged in particular by oxidizing or reducing treatments, i.e. for example by coloring with oxidation colorants, by bleaching with oxidizing agents or by shaping, for example by permanent waving or smoothing of the hair with strong keratin reducing agents, for example thioglycolate salts or sulfites.

Accordingly, the present invention also relates to a process for the oxidizing or reducing treatment of the hair in which, immediately after the oxidizing or reducing treatment step, the hair is treated with a composition containing a vitamin B6 derivative corresponding to formula I in a quantity of 0.05 to 2% by weight. This aftertreatment composition may be a shampoo, a rinse, a hair-care lotion, a setting lotion, a foam, a hair lotion or a spray, i.e. it may be either a rinse-off product or a leave-on product.

If the composition is applied after coloring of the hair, it may be, for example, a water-based hair-care lotion. If the aftertreatment is to be carried out after the reducing step of a permanent wave treatment, the vitamin B6 derivative may be added to the permanent wave fixing lotion. However, the aftertreatment may also be carried out after the permanent wave fixing step which is of course itself an oxidizing hair treatment. In this case, the vitamin B6 derivative is applied in the form of a hair-care lotion. The composition containing the vitamin B6 derivative is preferably used as a care lotion after oxidative coloring of the hair or for permanent wave fixing. Besides the vitamin B6 derivative, this preparation may contain any of the components which are typically used in the formulation of hair-care preparations and which are compatible with the hair or scalp.

The preparations used for oxidative fixing in permanent waving contain hydrogen peroxide, for example, as oxidizing agent and the stabilizers normally used to stabilize water-containing hydrogen peroxide preparations. The pH value of such aqueous $H_2O_2$ preparations which contain about 0.5 to 3% by weight of $H_2O_2$ is preferably between 2 and 4 and is adjusted with inorganic acids, preferably with phosphoric acid. However, the preferred oxidizing agent is sodium or potassium bromate. These bromates are used in a concentration of 1 to 10% by weight and the preparations are adjusted to a pH of 4 to 7.

Apart from the oxidizing agents, these permanent wave fixing lotions may contain other components, for example surfactants, quaternary ammonium salts, cationic polymers, water-soluble proteins or protein derivatives, perfumes, opacifiers, etc. A care lotion applied after permanent wave fixing may contain, for example, setting, conditioning, hair-care or antistatic components, alkaline earth metal or aluminium salts and other components.

The process according to the invention is particularly important for structurally improving hair keratin in conjunction with the oxidative coloring and/or bleaching of hair. Accordingly, in a particularly preferred embodiment, the present invention relates to a hair care lotion, more particularly for application after coloring or bleaching of the hair, characterized in that it contains 1 to 10% by weight of emulsified oil, fatty or wax components,
0.1 to 5% by weight of cationic surfactants,
0.2 to 2% by weight of a vitamin B6 derivative corresponding to formula I in a water-containing carrier.

Suitable oil or fatty components are paraffins, silicone oils, vegetable oils and animal fats (triglycerides), fatty acid fatty alcohol esters (wax esters), fatty acid esters of short-chain alcohols, dicarboxylic acid fatty alcohol esters, linear and branched-chain alcohols and diols containing 10 to 20 carbon atoms, fatty acid monoglycerides and other oils, fats or waxes.

Suitable cationic surfactants are compounds which contain a free or substituted amino group or quaternary ammonium group and, at the nitrogen atom, one or two relatively long-chain alkyl or acylaminoalkyl or acyloxyalkyl groups and up to three short-chain alkyl groups and optionally a benzyl group.

Examples of suitable quaternary ammonium surfactants are cetyl trimethyl ammonium chloride, lauryl dimethyl benzyl ammonium bromide, stearyl trimethyl ammonium chloride, distearoyloxyethyl dimethyl ammonium methoxysulfate, cocoacylaminopropyl trimethyl ammonmium chloride.

Other cationic surfactants are, for example, relatively long-chain primary, secondary or tertiary amines in the form of their salts, for example hydrochlorides or sulfates.

In addition to the components mentioned, the hair-care lotions according to the invention may contain, for example, nonionic surfactants and emulsifiers (for the oil and fatty component), water-soluble proteins, protein degradation products or protein derivatives, amino acids (for example serine), water-soluble cationic polymers, setting, film-forming polymers such as, for example, polyvinyl pyrrolidone, glucose and other structuring or scalp-care ingredients such as, for example, panthenol, tocopherol, allantoin, vegetable extracts such as, for example, birch or camomile extract, anti-dandruff agents, vitamins, for example vitamin B1 (thiamine), B2, (riboflavin), B3 (nicotinic acid, nicotinic acid amide), B7 (biotin), B12 (cyanocobalamine), C (ascorbic acid), E (tocopherol acetate), perfumes and UV protection factors.

UV protection factors are particularly important for the long-term protection of hair keratin against the harmful effects of the sun. Accordingly, in a preferred embodiment, the hair-care lotion according to the invention also contains a UV protection factor, preferably in the form of a substance which absorbs ultraviolet rays. Such substances are commercially available in large numbers as either water-soluble or lipid-soluble UV protection factors. In a preferred embodiment, the care lotion according to the invention contains a combination of water-soluble and lipid-soluble UV protection factors.

Suitable water-soluble UV protection factors are, for example, 2-hydroxy-4-methoxybenzophenone-5-sulfonic acid p-methoxycinnamic acid diethanolamine salt p-aminobenzoic acid 2-phenylbenzimidazole-5-sulfonic acid triethanolamine salicylate and lauryl-[3-(p-dimethylamainobenzamido)-propyl]-dimethyl ammonium-p-toluenesulfonate.

Suitable lipid-soluble UV protection factors are, for example, 2-hydroxy-4-methoxybenzopheneone 2-aminobenzoic acid menthyl ester 4-bis-(2-hydroxypropyl)-aminobenzoic acid ethyl ester 4-aminobenzoic acid-2,3-dihydroxypropyl ester 2-ethylhexyl-2-cyano-3,3-diphenyl acrylate p-methoxycinnamic acid-2-ethyl hexyl ester 4-methyl benzylidene camphor 4-tert.butyl-4'-methoxydibenzoyl methane.

The care lotion according to the invention is preferably an oil-in-water emulsion of the emulsified oil or fatty components which is either used for washing excess colorant out of the hair or which, after rinsing out of excess dye or excess bleaching agent with water, is applied to the hair in a separate step and uniformly distributed therein.

If the care lotion is to remain on the hair (leave-on product), the content of emulsified oil or fatty components is kept low, preferably below 3% by weight. However, rinsing with cold water is normally carried out after the treatment with the care lotion.

The following Examples are intended to illustrate the invention.

EXAMPLES

1. Demonstration of the Structuring Effect of Vitamin B6 in Topical Application 1.1 Method HP-DSC (High-Pressure Differential Scanning Calorimetry)

Thermoanalytical investigations are particularly suitable for characterizing two-phase systems to which human hair fibers as fibrous keratins with their crystalline α-helix component and amorphous matrix component also belong. On the one hand, glass transitions and aging behavior of the amorphous matrix can be investigated, on the other hand the melting behavior of the crystalline helical phase provides important information. Thermoanalytical studies were described for the first time in 1899. The first differential thermoanalyses (DTA) of protein fibers were carried out towards the end of the fifties (F. Schwenker, J. H. Dusenbury, Text. Res. J. 1963, 30, pages 800 et seq; W. D. Felix, M. A. McDowall, H. Eyring, ibid. (1963), 33, pages 465 et seq). In the following years, various thermoanalytical measuring techniques, such as DTA, HP-DTA (high-pressure DTA) and DSC (differential scanning calorimetry) were applied to keratin fibers, for example to investigate the phenomenon of supercontraction, α-β-phase transitions of the helices or denaturing processes. Recently, the method of IIP-DSC was used to study keratin fibers, more particularly at the Deutsches Wollforschungsinstitut (German Wool Research Institute) in Aachen (F. J. Wortmann, H. Deutz, J. Appl. Polym. Sci. 1993, 48, pp. 137 et seq.). IIP-DSC rules out the problems associated with pyrolytic effects which occur in conventional DSC and the problems with data acquisition and interpretation by which DTA is attended. DSC measurements are carried out on keratins which are encapsulated with water in commercially obtainable pressure-tight measuring capsules. In the keratin/water system, a high water vapor pressure from which the HP-DSC analysis derives builds up in the encapsulated steel crucibles on heating to >100° C. The crucial difference between the HP-DSC thermograms of human hair fibers and normal DSC thermograms is that the endothermal peaks which reproduce the transition point and the transition enthalpy are shifted by ca. 90° C. to lower temperatures. This derives from the fact that, after diffusing into the hair fibers, the water reduces protein stability by weakening and splitting hydrogen bridge bonds and salt bonds so that the "gluing temperature" of the keratins is reduced. If only hydrogen bridges and salt bridges are dissolved by the supercontracting agent, such as water, the thermal effect is reversible (supercontraction). However, the process becomes irreversible when covalent bonds, such as disulfide bridges for example, are split. This happens when human hair fibers are heated with water to >150° C. in pressure-tight capsules. The irreversible transition, interpreted as the transition of the α-helical regions in the proteins into a random state, results in endothermal peaks, the position of the peaks reproducing the transition point or even the denaturing point and their area reproducing the transition or denaturing enthalpy.

Accordingly, both structural and chemical states and changes in fiber keratins and particularly in human hair fibers can be detected by dynamic differential scanning calorimetry (DSC). Under precisely defined test conditions, the processes detectable by calorimetry in human hair fibers can be recorded in the form of thermograms and used in regard to peak positions, structures and areas as an indicator for influencing order/disorder transitions through changes in inner and/or outer parameters produced, for example, by cosmetic treatment of the hair fibers. In other words, information on the strength of or damage to human hair fibers can be obtained from the endothermal peaks recorded in the thermogram of human hair fibers on the basis of peak position (transition point) and peak area (transition enthalpy).

Detailed investigations into the influence of the cystine content on the denaturing of the α-helices in keratins have, for example, shown that the denaturing temperature (transition temperature) of the keratin increases linearly with the cystine content. The effect of the increased stability of the matrix region through the higher degree of crosslinking of the increased percentage of disulfide bridges in the matrix is that the transition of the helices embedded in this matrix is made difficult, resulting in an increase in the denaturing temperature. Conversely, a reduction in the denaturing temperature and above all in the denaturing enthalpy can generally be observed in human hair fibers treated by permanent waving or bleaching or coloring (H. Deutz, Doktorarbeit, RWTH Aachen 1993).

1.2 Procedure

Human hair (Alkinco 6633 and Alkinco 6634)) was intentionally damaged by permanent waving (commercial product Poly Lock extra starke Dauerwelle; 40 mins. permanent waving, 10 mins. fixing). Quantities of 0.5 g of tresses of both hair qualities were then treated for 10 mins. with a 1% aqueous solution of the active substances listed in Table 1 and, after rinsing, were dried. The active substances were then thermoanalytically tested for (re)structuring effects. The keratin melting points obtained are shown in Table 1.

TABLE 1

(Re)structuring by vitamin B6 and derivatives

| Active substance (1% in water) | Keratin melting point [° C.] for Alkinco 6633 | Keratin melting point [° C.] for Alkinco 6634 |
| --- | --- | --- |
| -, Permanent-waved reference sample | 143.5 | 149.8 |
| Pyridoxine | 144* | 152.1 |
| Pyridoxal | 147.7 | 152 |
| Pyridoxamine | 147.9 | 152.2 |
| Pyridoxal-5-phosphate | 148.3 | 152.7 |

Except for the increase in melting point by 0.5° C. by pyridoxine* in the case of Alkinco 6633, all effects are statistically highly significant.

The use of pyridoxine in an emulsion formulation (Application Example 3.1) also produced a (re)structuring effect which increased in dependence upon the concentration used. In this case, too, studies were carried out on human hair (Alkinco 6634) which, to demonstrate the desired effect, had been specifically predamaged as described above and then after-treated for 2 mins. with conditioner containing pyridoxine in various concentrations (Application Example 3.1). The results are set out in Table 2.

TABLE 2

(Re)structuring by vitamin B6 as a function of concentration

| Aftertreatment with conditioner + x % vitamin B6 | Keratin melting point [° C.] Alkinco 6634 |
| --- | --- |
| -, Permanent-waved reference sample | 145.6 |
| 0% | 145.9 |
| 0.2% | 146.2 |
| 0.5% | 146.5 |
| 1.0% | 147.4 |

Even the effect produced by the use of 0.2% of vitamin B6 is satistically significant by comparison with the reference sample.

2. Demonstration of the Improvement in the Fastness to Washing of Hair Colors

An improvement in the fastness to washing of hair colors, more particularly oxidation hair colors with red or violet reflex, by vitamin B6 and derivatives was demonstrated by the following tests:

Human hair fibers (Kerling Naturweiβ) were used. The hair fibers were intentionally damaged at their tips (2× blonding and 2× permanent waving) in order to simulate seriously damaged hair. The human hair fibers were colored a red-brown shade with an oxidative hair color (Poly Diadem 718—haselnut) in accordance with the directions for use, rinsed and then aftertreated for 5 mins. with a rinse (Application Example 3.2) containing 2% of active substance, i.e. vitamin B6 or derivative (reference with no active substance). After rinsing and drying, calorimetric measurements (hair shafts and tips separated) were carried out and were repeated after 6 washes. The values obtained for the overall color difference DE* (=color difference between sample or reference and corresponding unwashed, colored hair) are shown in Table 3. The smaller DE* is, the smaller the loss of color by shampooing and the higher the fastness to washing.

TABLE 3

Improvement in fastness to washing by vitamin B6 and derivatives

| Hair sample | DE* for normal weathered shafts | DE* for seriously damaged tips |
| --- | --- | --- |
| Colored, unwashed | 0 | 0 |
| Colored, conditioner without active aubstance, washed 6x | 3.2 | 8.7 |
| Colored, conditioner containing 2% vitamin B6, washed 6x | 1.8 | 5.8 |
| Colored, conditioner containing 2% pyridoxamine, washed 6x | 2.7 | 5.2 |

The increased fastness to washing of the hair colors is even clearly visible to the naked eye, particularly on the seriously damaged tips.

3. Application Examples (Hair-Care Lotions)

| Formulation | 3.1 | 3.2 |
| --- | --- | --- |
| Paraffin oil | 3.0% by weight | 2.5% by weight |
| Cetyl/stearyl alcohol | 3.0% by weight | 2.5% by weight |

-continued

| Formulation | 3.1 | 3.2 |
|---|---|---|
| Fatty alcohol ($C_{12-18}$) polyglycol ether (9.5 EO) | 0.2% by weight | 0.2% by weight |
| Palmitic acid cetyl ester | 0.8% by weight | 0.8% by weight |
| Beeswax | 0.05% by weight | — |
| Escalol ® HP 610 | 0.1% by weight | — |
| Uvinul ® M 40 | 0.5% by weight | — |
| Dehyquart ® A | 3.0% by weight | 3.0% by weight |
| Phenoxyethanol | 0.6% by weight | 0.6% by weight |
| Camomile distillate | 0.6% by weight | — |
| Methyl hydroxypropyl cellulose | 0.6% by weight | 0.6% by weight |
| pHB methyl ester | 0.2% by weight | 0.2% by weight |
| pHB propyl ester | 0.1% by weight | 0.1% by weight |
| Pyridoxine | 0–1.0% by weight | 2.0% by weight |
| Perfume | 0.3% by weight | 0.15% by weight |
| Water | to 100 (% by weight) | to 100 (% by weight) |

The following commercial products were used: Escalol® HP 610: dodecyl [3-(p-dimethylaminobenzamido)-propyl]-dimethylammonium-p-toluenesulfonate with propylene glycol monostearate (QUAT min. 65%, $H_2O$: 12–18%)
Uvinul® M40:2-hydroxy-4-methoxybenzophenone
Dehyquart® A: cetyl trimethyl ammonium chloride (25% in water)

What is claimed is:

1. A method for improving the structure and strength of hair keratin that is damaged by an oxidizing or reducing treatment and the fastness to washing of hair colors which comprises the steps of:
    applying to the hair keratin a topical application of a preparation containing a vitamin B6 derivative selected from the group consisting of pyridoxal, pyridoxal-5-phosphate and pyridoxamine or one of the corresponding physiologically compatible salts thereof, after the application of the oxidizing or reducing treatment, and then, rinsing the preparation from the hair keratin.

2. The method of claim 1 wherein the vitamin B6 derivative is present in the preparation in an amount of 0.05 to 2% by weight of the preparation.

3. The method of claim 2, wherein the preparation is used as a hair care lotion after oxidative coloring or for permanent wave fixing.

4. The method of claim 2 further comprising 1 to 10% by weight of emulsified oil, fatty or wax components, and 0.1 to 5% by weight of a cationic surfactant.

5. The method of claim 1 further comprising a protection factor in the form of a UV absorber.

* * * * *

UNITED STATES PATENT AND TRADEMARK OFFICE
CERTIFICATE OF CORRECTION

PATENT NO. : 6,787,128 B2
DATED : September 7, 2004
INVENTOR(S) : Kleen et al.

It is certified that error appears in the above-identified patent and that said Letters Patent is hereby corrected as shown below:

Column 10,
Line 22, after the word "surfactant", add -- in a water containing carrier. --

Signed and Sealed this

First Day of February, 2005

JON W. DUDAS
*Director of the United States Patent and Trademark Office*